United States Patent [19]

Zinnen

[11] Patent Number: 4,467,126
[45] Date of Patent: Aug. 21, 1984

[54] PROCESS FOR THE SEPARATION OF DI-SUBSTITUTED BENZENE

[75] Inventor: Hermann A. Zinnen, Evanston, Ill.

[73] Assignee: UOP Inc., Des Plaines, Ill.

[21] Appl. No.: 515,001

[22] Filed: Jul. 18, 1983

[51] Int. Cl.³ .................... C07C 79/12; C07C 79/10
[52] U.S. Cl. ............................. 568/937; 210/670; 260/465 R; 564/424; 568/932; 568/940
[58] Field of Search ............... 260/465 R; 564/424; 568/932–937, 940; 210/670

[56] References Cited

U.S. PATENT DOCUMENTS

| | | | |
|---|---|---|---|
| 2,985,589 | 5/1961 | Broughton et al. | 210/34 |
| 3,114,782 | 12/1963 | Fleck et al. | 260/674 |
| 3,201,491 | 8/1965 | Stine et al. | 260/676 |
| 3,558,732 | 1/1971 | Neuzil | 260/674 |
| 3,668,267 | 6/1972 | Hedge | 260/674 |
| 3,686,342 | 8/1972 | Neuzil | 260/674 |
| 3,997,620 | 12/1976 | Neuzil | 260/674 |
| 4,234,520 | 11/1980 | Priegnitz | 568/937 |
| 4,240,986 | 12/1980 | Priegnitz | 568/937 |
| 4,270,013 | 5/1981 | Priegnitz et al. | 568/940 |

Primary Examiner—Leland A. Sebastian
Attorney, Agent, or Firm—James R. Hoatson, Jr.; Louis A. Morris; William H. Page, II

[57] ABSTRACT

An adsorptive separation process for separating the para-isomers of a di-substituted benzene from a feed mixture comprising the para-isomer and at least one other isomer. One substituted group is $NO_2-$ and the other group is a normal hydrocarbon having less than 6 carbon atoms per molecule, the halogens, $NH_2-$, $NO_2-$ or $C\equiv N-$. The process comprises contacting the feed mixture with an adsorbent comprising crystalline silica having a silica/alumina mole ratio of at least 12, selectively adsorbing substantially all of the para-isomer to the substantial exclusion of the remaining isomers and thereafter recovering high-purity para-isomer by means of desorption with an appropriate desorbent material.

10 Claims, 6 Drawing Figures

PROCESS FOR THE SEPARATION OF DI-SUBSTITUTED BENZENE

BACKGROUND OF THE INVENTION

1. Field of the Invention

The field of art to which the claimed invention pertains is solid bed adsorptive separation. More specifically, the claimed invention relates to a process for the separation of di-substituted benzene isomers from a feed mixture comprising such isomers, which process employs a solid adsorbent which selectively removes the paraisomer from the feed mixture, thereby producing a fluid raffinate stream comprising a mixture of the nonadsorbed isomers.

2. Description of the Background Information

It is well known in the separation art that certain crystalline aluminosilicates can be used to separate hydrocarbon species from mixtures thereof. The separation of normal paraffins from branched-chained paraffins, for example, can be accomplished by using a type A zeolite which has pore openings from 3 to about 5 angstroms. Such a separation process is disclosed in U.S. Pat. Nos. 2,985,589 and 3,201,491. These adsorbents allow a separation based on the physical size differences in the molecules by allowing the smaller or normal hydrocarbons to be passed into the cavities within the zeolitic adsorbent, while excluding the larger or branched chain molecules.

In addition to separating hydrocarbon types, the type X or type Y zeolites have also been employed in processes to separate individual hydrocarbon isomers. In the process described in U.S. Pat. No. 3,114,782, for example, a particular zeolite is used as an adsorbent to separate alkyl-trisubstituted benzene; and in U.S. Pat. No. 3,668,267, a particular zeolite is used to separate specific alkyl-substituted naphthalenes. In processes described in U.S. Pat. Nos. 3,558,732; 3,686,342 and 3,997,620, adsorbents comprising particular zeolites are used to separate para-xylene from feed mixtures comprising para-xylene and at least one other xyklene isomer by selectively adsorbing para-xylene over the other xylene isomers. In the last mentioned processes, the adsorbents used are para-xylene selective; para-xylene is selectively adsorbed and recovered as an extract component while the rest of the xylenes and ethylbenzenes are all relatively unadsorbed with respect to para-xylene and are recovered as raffinate components. Also, in the last mentioned processes, the adsorption and desorption may be continuously in a simulated moving bed countercurrent flow system, the operating principles and sequence of which are described in U.S. Pat. No. 2,985,589.

The effectiveness of type X and Y zeolites for separating isomers of nitrotoluene is disclosed in U.S. Pat. No. 4,270,013. The highest silica/alumina mole ratio obtained with this type of zeolite, i.e. type Y, is 8.

I have discovered that a crystalline silica adsorbent having a silica/alumina mole ratio of at least 12 is highly effective in separating the para isomer of certain di-substituted benzenes from the other isomers, particularly when used with specific desorbent materials.

SUMMARY OF THE INVENTION

It is accordingly a broad objective of my invention to provide a process for the separation of high purity para-isomers at high recoveries from a feed mixture comprising the isomers of di-substituted benzene, one substituted group being $NO_2$—and the other substituted group being selected from the group consisting of normal hydrocarbons having less than 6 carbon atoms per molecule, the halogens, $NH_2$—, $NO_2$—, and $C\equiv N$—. Recovery is effected by desorption of the para-disubstituted benzene with a desorbent material comprising a nitrile or nitro-substituted monocyclic aromatic or alkane in mixture with a monocyclic aromatic carrier material.

In brief summary, the present invention is a process for separating the above para-isomers from their respective feed mixtures comprising the para-isomer and at least one other isomer. The process comprises contacting, at adsorption conditions, the mixture with an adsorbent comprising crystalline silica having a silica/alumina mole ratio of at least 12, selectively adsorbing the para-isomer to the substantial exclusion of the remaining isomers, removing the remaining isomers from the adsorbent, and thereafter recovering high-purity para-isomer.

Other objectives and embodiments of the present invention encompass details about feed mixtures, adsorbents, desorbent materials and operating conditions, all of which are hereinafter disclosed in the following discussion of each of the facets of the present invention.

DESCRIPTION OF THE INVENTION

At the outset the definitions of various terms used throughout the specification will be useful in making clear the operation, objects and advantages of this process.

A "feed mixture" is a mixture containing one or more extract components and one or more raffinate components to be separated by this process. The term "feed stream" indicates a stream of a feed mixture which passes to the adsorbent used in the process.

An "extract component" is a component that is more selectively adsorbed by the adsorbent while a "raffinate component" is a component that is less selectively adsorbed. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream, and preferably at least a portion of the raffinate stream, from the separation process are passed to separation means, typically fractionators or evaporators, where at least a portion of desorbent material is separated to produce an extract product and a raffinate product. the term "extract product" and "raffinate product" mean products produced by the process containing, respectively, an extract component and a raffinate component in higher concentrations than those found in the extract stream and the raffinate stream.

The term "selective pore volume" of the adsorbent is defined as the volume of the adsorbent which selectively adsorbs an extract component from the feed mixture. The term "non-selective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent. When adsorbent "passes" into an operational zone (hereinafter defined and described) employed in one embodiment of this process, its non-selective void volume, together with its selective pore volume, carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in non-selective void volume of the adsorbent, it, in most instances, comprises less selectively retained feed components. The selective pore volume of an adsorbent can in certain instances adsorb portions of raffinate material from the fluid surrounding the adsorbent, since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

The prior art has recognized that certain characteristics of adsorbents are highly desirable, if not absolutely necessary, to the successful operation of a selective adsorption process. Such characteristics are equally important to this process. Among such characteristics are: adsorptive capacity for some volume of an extract component per volume of adsorbent; the selective adsorption of an extract component with respect to a raffinate component and the desorbent material; and sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of a separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another, but can also be expressed between any feed mixture component and the desorbent material. The selectivity, (B), is defined as the ratio of the two components of the adsorbed phase over the ratio of the same two components in the unadsorbed phase at equilibrium conditions. Relative selectivity is shown as Equation 1, below:

Equation 1
$$\text{Selectivity} = (B) = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0, there is no preferential adsorption of one component by the adsorbent with respect to the other; they are both adsorbed (or non-adsorbed) to about the same degree with respect to each other. As the (B) becomes less than or greater than 1.0, there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is just slightly greater than 1.0, it is preferred that such selectivity be reasonably greater than 1.0. Like relative volatility, the higher the selectivity, the easier the separation is to perform. Higher selectivities permit a smaller amount of adsorbent to be used. The third important characteristic is the rate of exchange of the extract component of the feed mixture material, or, in other words, the relative rate of desorption of the extract component. This characteristic relates directly to the amount of desorbent material that must be employed in the process to recover the extract component from the adsorbent; faster rates of exhange reduce the amount of desorbent material needed to remove the extract component and therefore permit a reduction in the operating cost of the process. With faster rates of exchange, less desorbent material has to be pumped through the process and separated from the extract stream for reuse in the process.

The adsorbent to be used in the process of this invention comprises crystalline silica having a silica/alumina mole ratio of at least 12. One such crystalline silica is known as silicalite which has a silica/alumina mole ratio of infinity, i.e., it contains no alumina. Silicalite is a hydrophobic crystalline silica molecular sieve. Silicalite is disclosed and claimed in U.S. Pat. Nos. 4,061,724 and 4,104,294 to Grose et al., incorporated herein by reference. Due to its aluminum-free structure, silicalite does not show ion-exchange behavior, and is hydrophobic and organophilic. Silicalite is uniquely suitable for the separation process of this invention for the presumed reason that its pores are of a size and shape that enable the silicalite to function as a molecular sieve, i.e., accept the molecules of para-isomer into its channels of internal structure, while rejecting the molecules of the other isomers. A more detailed discussion of silicalite may be found in the article, "Silicalite, A New Hydrophobic Crystalline Silica Molecular Sieve"; *Nature*, Vol. 271, Feb. 9, 1978, incorporated herein by reference.

Examples of other crystalline silicas suitable for use in the present invention are those having the trademark designation "ZSM" and silica/alumina mole ratios of at least 12. The ZSM adsorbents are as described in U.S. Pat. No. 4,309,281 to Dessau, incorporated herein by reference.

Typically, adsorbents used in separative processes contain the crystalline material dispersed in an amorphous material or inorganic matrix. The crystalline material will typically be present in the adsorbent in amounts ranging from about 75 to about 98 wt. % based on volatile-free composition. Volative-free compositions are generally determined after the adsorbent has been calcined at 900° C. in order to drive off all volatile matter. The remainder of the adsorbent will generally be the inorganic matrix material such as silica, titania, or alumina or mixtures thereof, or compounds, such as clays, which material is present in intimate mixture with the small particles of the crystalline material. The usual purpose of this matrix material is a binder to aid in forming or agglomerating the hard crystalline particles of the crystalline material. Normally, the adsorbent will be in the form of particles such as extrudates, aggregates, tablets, macrospheres or granules having a desired particle size range. The typical adsorbent will have a particle size range of about 16–60 mesh (Standard U.S. Mesh).

Desorbent materials used in various prior art adsorptive separation processes vary depending upon such factors as the type of operation employed. In the swing bed system, in which the selectively adsorbed feed component is removed from the adsorbent by a purge stream, desorbent selection is not a critical and desorbent material comprising gaseous hydrocarbons such as methane, ethane, etc., or other types of gases such as nitrogen or hydrogen, may be used at evaporated temperatures or reduced pressures or both to effectively purge the adsorbed feed component from the adsorbent. However, in adsorptive separation processes which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the above discussed selectivity, it is preferred that the adsorbent be more selective for all of the extract components with respect to a raffinate component than it is for the desorbent material with respect to a raffinate component. Secondly, desorbent material must be compatible with the particular adsorbent and the particular feed mixture. More specifically, they must not reduce or destroy the critical selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent in admixture with desorbent material and any chemical reaction involving a desorbent material and an extract component or a raffinate component would reduce the purity of the extract product or the raffinate product or both. Since both the raffinate stream and the extract stream typically contain desorbent material, desorbent materials should additionally be substances which are easily separable from the feed mixture that is passed into the process. Without a method of separating at least a portion of the desorbent material present in the extract stream and the raffinate stream, the concentration of an extract component in the extract product and the concentration of a raffinate component in the raffinate product would not be vary high, nor would the desorbent material be available for reuse in the process. It is contemplated that at least a portion of the desorbent material will be separated from the extract and the raffinate streams by distillation or evaporation, but other separation methods such as reverse osmosis may also be employed alone or in combination with distillation or evaporation. Finally, desorbent materials should also be materials which are readily available and therefore reasonable in cost.

The desorbent material found to be effective when used with the adsorbent of the present invention is a nitrile or nitro substituted monocyclic aromatic or alkane in mixture with a monocyclic aromatic carrier material. Particularly preferred mixtures are nitrobenzene and toluene, acetonitrile and mesitylene, and nitromethane and mesitylene.

The adsorbent may be employed in the form of a dense compact fixed bed which is alternatively contacted with the feed mixture and desorbent materials. In the simplest embodiment of the invention, the adsorbent is employed in the form of a single static bed in which case the process is only semi-continuous. In another embodiment, a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Moving bed or simulated moving bed flow systems, however, have a much greater separation efficiency than fixed adsorbent bed systems and are therefore preferred for use in this separation process. In the moving bed or simulated moving bed processes, the adsorption and desorption operations are continuously taking place which allows both continuous production of an extract and a raffinate stream and the continual use of feed and desorbent streams. One preferred embodiment of this process utilizes what is known in the art as the simulated moving bed countercurrent flow sytem. The operating principles and sequence of such a flow system are described in U.S. Pat. No. 2,985,589 incorporated herein by reference thereto. In such a system, it is the progressive movement of multiple liquid access points down an adsorbent chamber that simulates the upward movement of adsorbent contained in the chamber. Only four of the access lines are active at any one time: the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of this process, it is generally necessary that three separate operational zones be present in order for the process to take place although in some instances an optional fourth zone may be used.

Figure 1:
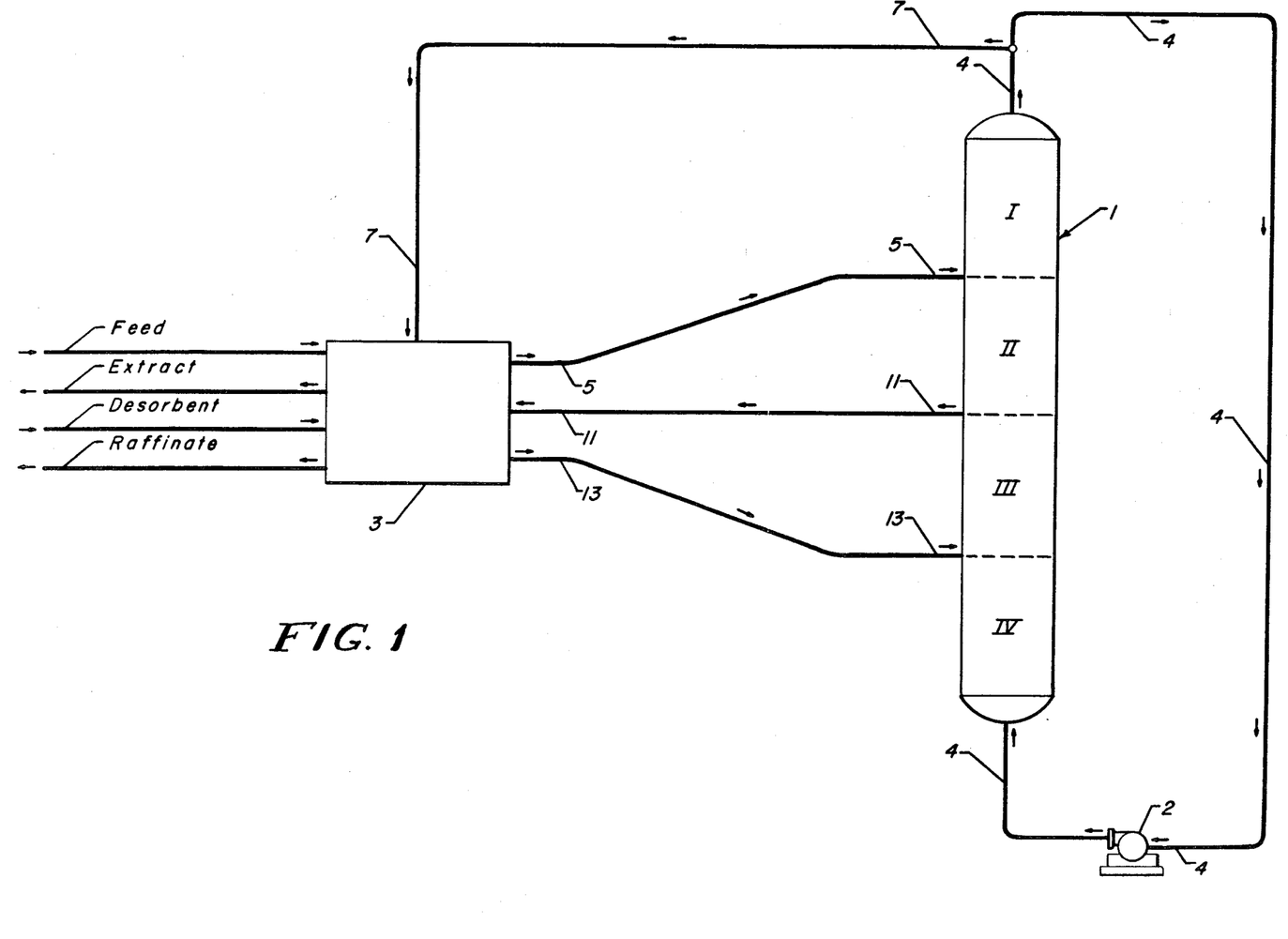
FIG. 1 represents, in schematic form, an embodiment of the present invention incorporating a simulated moving bed, hereinafter described, including adsorption column 1, manifold system 3 and various interconnecting lines.

There is a net positive fluid flow through all portions of the column in the same direction, although the composition and rate of the fluid will, of course, vary from point to point. With reference to FIG. 1, zones I, II, III and IV are shown as well as manifold system 3, pump 2, which maintains the net positive fluid flow, and line 4 associated with pump 2. Also shown and identified are the inlet and outlet lines to the process which enter or leave via manifold system 3.

The adsorption zone, zone I, is defined as the adsorbent located between the feed inlet streams and the raffinate outlet stream 7. In this zone, the feedstock contacts the adsorbent, an extract component is adsorbed, and a raffinate stream is withdrawn. Since the general flow through zone I is from the feed stream which passes into the zone to the raffinate stream which passes out of the zone, the flow in this zone is considered to be in a downstream direction when proceeding from the feed inlet to the raffinate outlet streams Immediately upstream with respect to fluid flow in zone I is the purification zone, zone II. The purification zone is defined as the adsorbent between the extract outlet stream 11 and the feed inlet streams. The basic operations taking place in zone II are the displacement from the non-selective void volume of the adsorbent of any raffinate material carried into zone II by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone III into zone II at zone II's upstream boundary, the extract outlet stream, to effect the displacement of raffinate material. The flow of material in zone II is in a downstream direction from the extract outlet stream to the feed inlet stream.

Immediately upstream of zone II with respect to the fluid flowing in zone II is the desorption zone, or zone III. The desorption zone is defined as the adsorbent between the desorbent inlet 13 and the extract outlet stream 11. The function of the desorption zone is to allow a desorbent material which passes into this zone to displace the extract component which was retained in the adsorbent during a previous contact with feed in zone I in a prior cycle of operation. The flow of fluid in zone III is essentially in the same direction as that of zones I and II.

In some instances, an optional buffer zone, zone IV, may be utilized. This zone, defined as the adsorbent between the raffinate outlet stream 7 and the desorbent inlet stream 13, if used, is located immediately upstream with respect to the fluid flow to zone III. Zone IV would be utilized to conserve the amount of desorbent utilized in the desorption step since a portion of the raffinate stream which is removed from zone I can be passed into zone IV to displace desorbent material present in that zone out of that zone into the desorption zone. Zone IV will contain enough adsorbent so that raffinate material present in the raffinate stream passing out of zone I and into zone IV can be prevented from passing into zone III, thereby contaminating the extract stream removed from zone III. In the instances in which the fourth operational zone is not utilized, the raffinate stream passing from zone I to zone IV must be carefully monitored in order that the flow directly from zone I to zone III can be stopped when there is an appreciable quantity of raffinate material present in the raffinate stream passing from zone I into zone III so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams, thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically, rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent, that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternatively and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent stream which can be reused in the process and a raffinate product containing a reduced concentration of desorbent material. The separation means will typically be a fractionation column or an evaporator, the design and operation of either being well known to the separation art.

Reference can be made to D. B. Broughton U.S. Pat. No. 2,985,589, and to a paper entitled "Continuous Adsorptive Processing—A New Separation Technique" by D. B. Broughton presented at the 34th Annual Meeting of the Society of Chemical Engineers at Tokyo, Japan, on Apr. 2, 1969 (both of which are incorporated herein by reference), for further explanation of the simulated moving bed countercurrent process flow scheme.

Another type of simulated moving bed system is the cocurrent system set forth in patent application Ser. No. 407,680, filed Aug. 12, 1982, incorporated by reference herein in its entirety, entitled "High Efficiency Continuous Separation Process."

The size of the units which can utilize the process of this invention can vary anywhere from those of pilot plant scale (see for example our assignee's U.S. Pat. No. 3,706,812) to those of commercial scale and can range in flow rates from as little as a few cc an hour up to many thousands of gallons per hour.

Adsorption and desorption conditions for adsorptive separation processes can generally be either in the liquid or vapor phase or both but for aromatic isomer separation processes employing crystalline adsorbents all liquid-phase operations are usually preferred because of the lower temperature requirements and the slightly improved selectivities associated with the lower temperatures. Preferred adsorption conditions for the process of this invention will include temperatures within the range of from about 40° C. to about 230° C. and will include pressures sufficient to maintain liquid phase. Desorption conditions for the process of the invention shall generally include the same range of temperatures and pressures as described for adsorption operations. The desorption of the selectively adsorbed isomer could also be effected at subatmospheric pressures or elevated temperatures or both or by vacuum purging of the adsorbent to remove the adsorbed isomer but this process is not directed to these desorption methods.

A dynamic testing apparatus may be employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to detect qualitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed which may contain known concentrations of a non-adsorbed tracer and of isomers of the di-substituted benzene, all diluted in desorbent, is injected for a duration of several minutes. Desorbent flow is resumed, and the tracer and the isomers are eluted as in a liquid-solid chromatographic operation. The effluent is collected in fractions and analyzed using chromatographic equipment and traces of the envelopes of corresponding components peaks developed.

From information derived from the test, adsorbent performance can be rated in terms of retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope. The rate of exchange of an extract component with the desorbent can generally be characterized by the width of the peak envelopes at half intensity. The narrower the peak width the faster the desorption rate.

Selectivity, (B), with regard to two given components, is equal to the quotient obtained by dividing the respective retention volumes of such components. Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1.0, it is preferred that such selectivity be greater than 2.0. Like relative volatility, the higher the selectivity the easier the separation is to perform. Higher selectivities permit a smaller amount of adsorbent to be used. The rate of exchange relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

The examples shown below are intended to further illustrate the process of this invention and are not to be construed as unduly limiting the scope and spirit of said process. The examples present dynamic test results for various adsorbent-desorbent combinations using the above described pulse test apparatus.

EXAMPLE I

In this example, the pulse test column was packed with clay bound silicalite, the feed stream comprised 10 wt. % of each nitrotoluene isomer dissolved in desorbent which comprised 15 wt. % acetonitrile in toluene. The flow was up the column at a rate of 1.1 cc per min. The column temperature was 150° C.

Feed was injected into the column in 2.6 cc pulses. There was mesitylene added to the feed to serve as a tracer in an amount comprising 10 wt. % of the feed stream.

Figure 2:
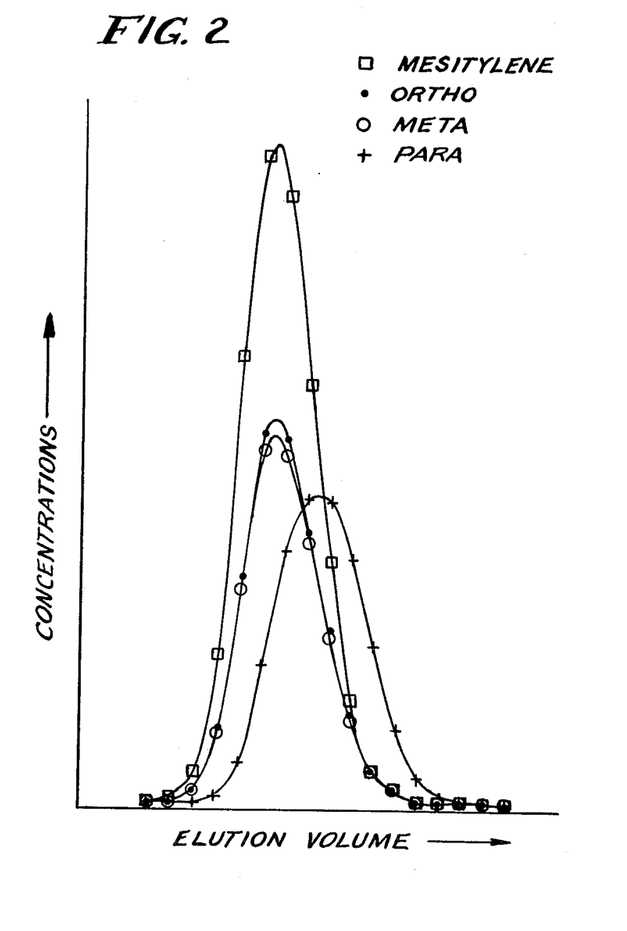
FIGS. 2 through 6 comprise graphical representations of data obtained for the following examples.

The results of this pulse test are shown in FIG. 2 which comprises plots of the analysis of fractions collected from the column for isomer content.

The results of the test as shown in FIG. 2 show that separation of para-nitrotoluene from the other isomers occurred, but it is rather mediocre in that the ortho and meta isomer curves tail significantly into the para curve.

A further observation is that since the meta and ortho isomers eluted with the tracer, i.e., as part of the void volume, the indication is that those isomers are totally rejected by the adsorbent. Relative selectivity (B) for the para isomer could therefore be considered infinite. Tracers were not used in the subsequent tests since the ortho and meta isomers functioned as such.

The following retention volume for the nitrotoluene isomers were calculated from the curves:

| ortho | 0.0 |
|---|---|
| meta | 0.0 |
| para | 3.6 |

EXAMPLE II

In this example, all details of Example I were repeated except that the adsorbent was 15 wt. % nitrobenzene in toluene and the flow rate up the column was 1.2 cc per min.

Figure 3:
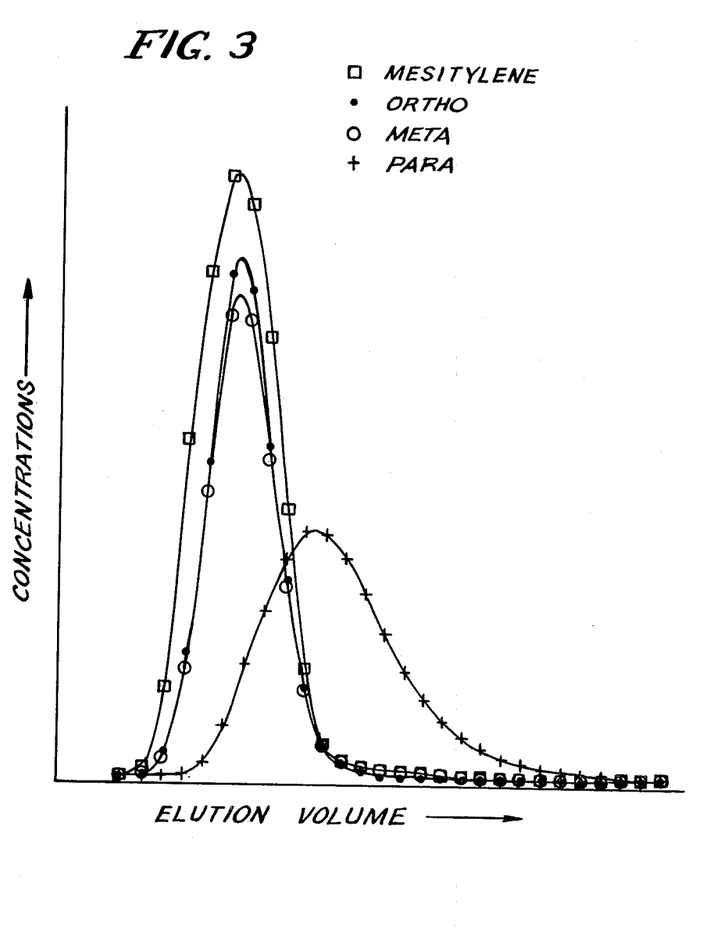

The results of the pulse test for this example are shown in FIG. 3. FIG. 3 shows a significant separation of paranitrotoluene from the other isomers, with very little tailing by the latter into the former.

The calculated retention volumes were as follows:

| ortho | 0.0 |
|---|---|
| meta | 0.0 |
| para | 8.5 |

EXAMPLE III

In this example, all details of Example II were repeated except that the desorbent was 15 wt. % of acetonitrile in mesitylene.

Figure 4:
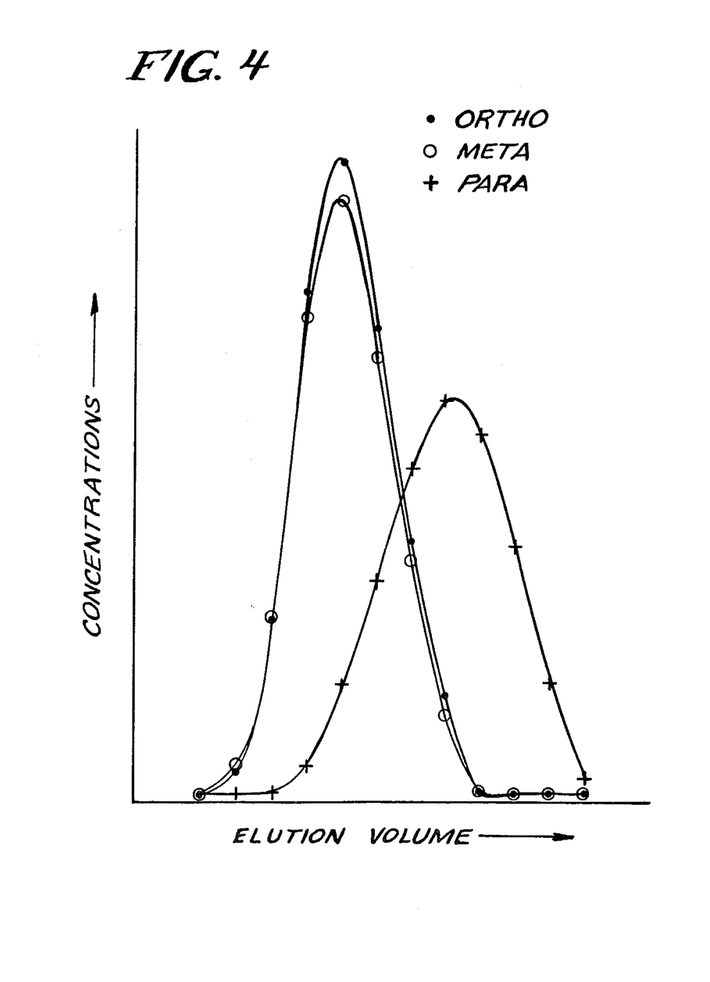

The results of the pulse test for this example are shown in FIG. 4. FIG. 4 shows another significant separation of paranitrotoluene from the other isomers.

The calculated retention volumes were as follows:

| ortho | 0.0 |
|---|---|
| meta | 0.0 |
| para | 6.75 |

EXAMPLE IV

In this example, all details of Example III were repeated except that the desorbent was 15 wt. % of nitromethane in mesitylene and the flow rate up the colmun was 1.18 cc per min.

Figure 5:
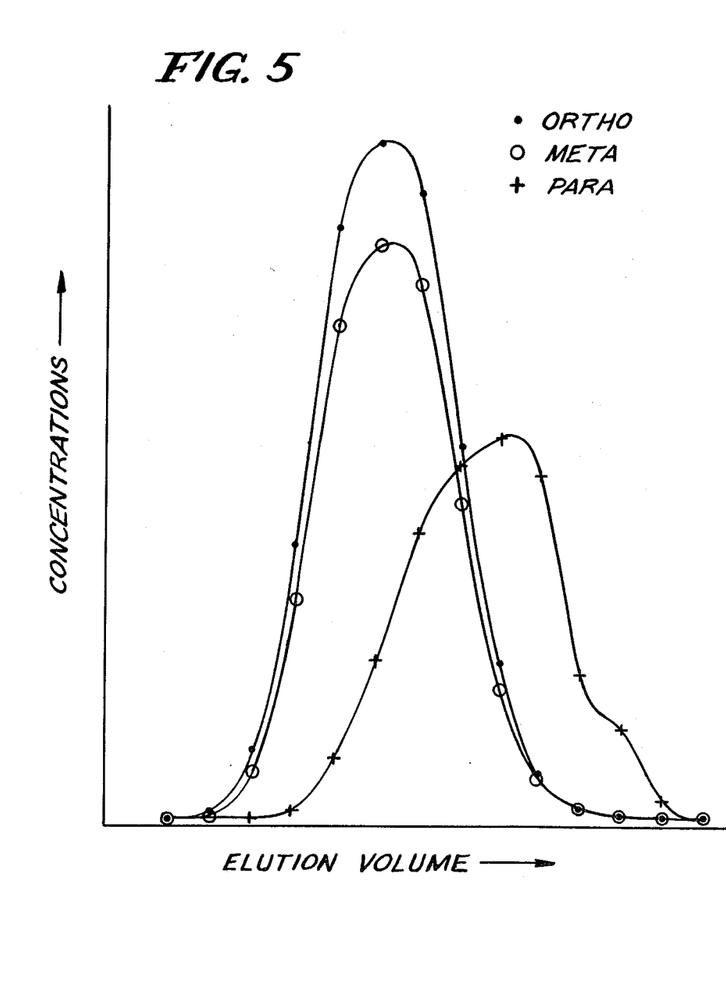

The results of the pulse test for this example are shown in FIG. 5. FIG. 5 shows a definite separation between th para and other isomers, although not as good as that shown in previous examples.

The calculated retention volumes were as follows:

| ortho | 0.0 |
|---|---|
| meta | 0.0 |
| para | 4.25 |

EXAMPLE V

In this example, the isomers separated were those of chloronitrobenzene, a species of feedstock different from the feedstocks of the previous example, but within the scope of the present invention as claimed. The feed stream was 0.5 gram of each isomer in 3.5 grams of desorbent. The desorbent used was butyronitrile in mesitylene. The flow rate up the column was 1.2 cc per min. All other details were the same as for the previous examples.

Figure 6:
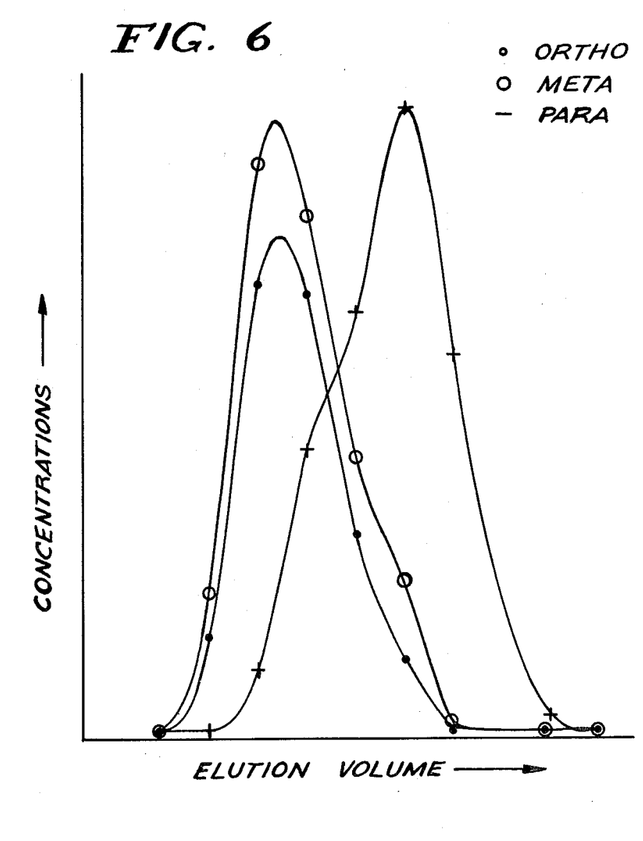

The results of the pulse test for this example are shown in FIG. 6. FIG. 6 shows an excellent separation between the para and other isomers of the chloronitrobenzene.

The calculated retention volumes were as follows:

| ortho | 0.0 |
|---|---|
| meta | 0.0 |
| para | 4.1 |

I claim as my invention:

1. A process for separating the para-isomer of a di-substituted benzene, one substituted group being $NO_2-$ and the other substituted group being selected from the group consisting of normal hydrocarbons having less than 6 carbon atoms per molecule, the halogens, $NH_2-$, $NO_2-$ and $C\equiv N-$ from a feed mixture comprising said para-isomer and at least one other isomer of said di-substituted benzene, which process comprises contacting at adsorption conditions said mixture with an adsorbent comprising crystalline silica having a silica/alumina mole ratio of at least 12, selectively adsorbing said para-isomer to the substantial exclusion of the remaining isomers, removing the remaining isomers from said adsorbent and thereafter recovering high-purity paraisomer by desorption with a desorbent material comprising a nitrile or nitro-substituted monocyclic aromatic or alkane in mixture with a monocyclic aromatic carrier material.

2. The process of claim 1 wherein said feed mixture comprises para-nitrotoluene and at least one of the isomers, meta-nitrotoluene, and ortho-nitrotoluene.

3. The process of claim 1 further characterized in that said desorbent material has an average boiling point substantially different from that of the feed mixture.

4. The process of claim 2 wherein said desorbent material comprises a mixture of nitrobenzene and toluene.

5. The process of claim 2 wherein said desorbent material comprises a mixture of acetonitrile and mesitylene.

6. The process of claim 2 wherein said desorbent material comprises a mixture of nitromethane and mesitylene.

7. The process of claim 1 wherein said feed mixture comprises para-chloronitrobenzene and at least one of the isomers meta-chloronitrobenzene and ortho-chloronitrobenzene.

8. The process of claim 7 wherein said desorbent material comprises butyronitrile and mesitylene.

9. The process of claim 1 further characterized in that said adsorption conditions include a temperature within the range of from about 40° C. to about 230° C. and at a pressure sufficient to maintain liquid phase.

10. The process of claim 1 wherein said process is effected by a simulated moving bed flow system.

* * * * *